United States Patent [19]
Barnard

[11] 3,964,998
[45] June 22, 1976

[54] IMPROVEMENTS IN AND RELATING TO WASTE WATER TREATMENT

[75] Inventor: James Laing Barnard, Pretoria, Transvaal, South Africa

[73] Assignee: The South African Inventions Development Corporation, Pretoria, Transvaal, South Africa

[22] Filed: Apr. 9, 1975

[21] Appl. No.: 566,362

Related U.S. Application Data

[63] Continuation of Ser. No. 377,390, July 9, 1973, abandoned.

[30] Foreign Application Priority Data

Aug. 4, 1972 South Africa.................... 72/5371

[52] U.S. Cl. ........................................ 210/7; 210/8; 210/16; 210/DIG. 27
[51] Int. Cl.² ........................................ C02C 1/06
[58] Field of Search .................... 210/3–8, 210/11, 16, 17, 18, 195, DIG. 27

[56] References Cited
UNITED STATES PATENTS

| | | | |
|---|---|---|---|
| 2,348,126 | 5/1944 | Green | 210/195 |
| 2,419,492 | 4/1947 | Green | 210/5 |
| 2,436,584 | 2/1948 | Logan | 210/5 |
| 2,529,295 | 11/1950 | Hood | 210/7 |
| 3,579,439 | 5/1971 | Meiring et al. | 210/5 |
| 3,617,540 | 11/1971 | Bishop et al. | 210/16 |
| 3,654,147 | 4/1972 | Levin et al. | 210/16 |
| 3,709,364 | 1/1973 | Savage | 210/195 |
| 3,764,523 | 10/1973 | Stankewich | 210/5 |
| 3,817,857 | 6/1974 | Torpey | 210/3 |
| 3,900,394 | 8/1975 | Rongred | 210/16 |

Primary Examiner—Thomas G. Wyse

[57] ABSTRACT

A process for removing nitrogen from raw or settled sewage, comprising passing the sewage through a first stage in the form of an anoxic biological denitrification stage, through a second stage in the form of an aerated biological nitrification stage, through a third stage in the form of an anoxic biological denitrification stage, through a fourth stage in the form of an aeration stage to facilitate solids separation, through a solids separation stage to provide a clarified effluent and an active sludge, of recycling mixed liquor from the second stage to the first stage and of recycling at least portion of the active sludge to the first stage. The process adapted for the additional removal of phosphates by regularly wasting sludge, by aerating the fourth stage to maintain a dissolved oxygen concentration of at least 4 mg/l, and by controlling th sludge recycle rate to limit the sludge retention time in the solids separation stage. Apparatus for carrying out the process comprising apparatus stages which correspond to the process stages, and feed means for feeding mixed liquor between the stages, mixed liquor recycling means and active sludge recycling means.

18 Claims, 7 Drawing Figures

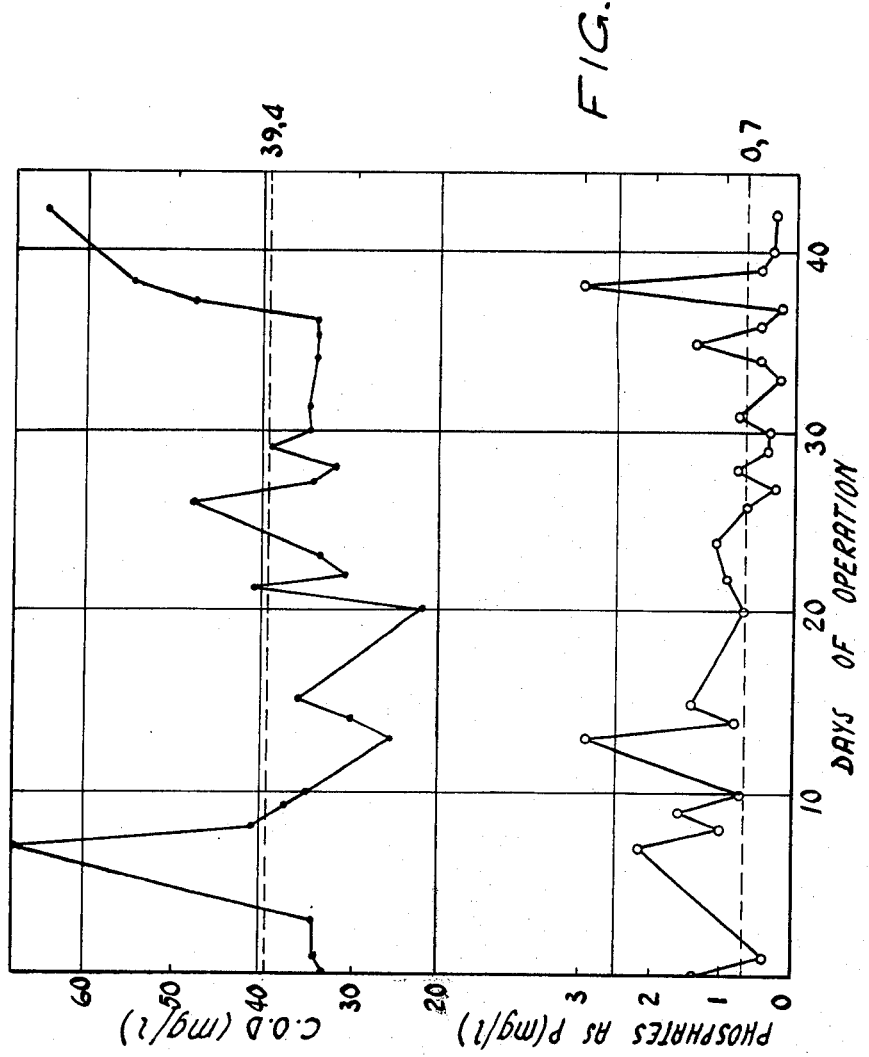

IMPROVEMENTS IN AND RELATING TO WASTE WATER TREATMENT

This is a continuation of application Ser. No. 377,390, filed July 9, 1973, now abandoned.

This invention relates to improvements in and relating to waste water treatment. More particularly this invention relates to the treatment of organic waste water containing nitrogenous compounds in dissolved and/or suspended form, for the removal of nitrogen. Another aspect of this invention relates to the treatment of organic waste water containing nitrogenous compounds and phosphates, for the removal of nitrogen and phosphate.

In accordance with the invention a process for removing nitrogen from organic waste water containing nitrogenous compounds, includes the step of passing the organic waste water through a first stage comprising a biological denitrification stage, through a second stage comprising a biological nitrification stage, through a third stage comprising a biological denitrification stage, through a solids separation stage to provide a clarified effluent and an active sludge, of recycling mixed liquor from the second stage to the first stage and of recycling at least portion of the active sludge to the first stage.

Insofar as the first and third stages are concerned, while the mechanism of biological denitrification is not yet fully understood, it is generally accepted that a considerable number of facultative bacteria which exist in normal activated sludge, appear to transfer electrons to nitrite and nitrate instead of oxygen in the respiration chain when the oxygen tension is sufficiently low. In other words, the nitrates and nitrites replace oxygen as the final electron acceptors in the respiration chain as soon as the oxygen tension drops sufficiently. In doing so they are reduced to nitrogen gas, $N_2O$ gas and other minor forms of nitrogenous gas.

Since the electronic pathway is the same as in normal respiration under aerobic conditions, except for the last electron transfer from the cytochromes to the final acceptor, it is implied that all the substrates normally used by the cells for respiration may serve as hydrogen donors for the reduction of nitrates and nitrites.

It is believed therefore that the cell mass under low oxygen tension conditions would be little different from that under aerobic conditions and the rates of substrate breakdown should not be affected. Thus cell growth rates can be expected to be similar to that of aerobic processes.

Denitrification processes therefore require that nitrate containing effluents be mixed or contacted under anaerobic conditions, with a bacterial population having a sufficient respiration rate to affect denitrification in a reasonable time. The bacterial population may be in suspension, may be growing on submerged media, or the like.

Where a denitrification process is operated under anaerobic conditions, if the supply of oxygen, nitrates and nitrites becomes insufficient, sulphate reduction and anaerobic fermentation can occur.

The first and third stages of this invention should therefore conveniently be operated under those conditions where nitrates and nitrites serve as the final electron acceptors in the respiration chain of the facultative bacteria, but without sulphate reduction or anaerobic fermentation occurring. Such conditions will hereinafter be referred to as "anoxic conditions".

In the process of this invention therefore, if conditions in the first stage become so anaerobic that sulphate reduction or anaerobic fermentation occurs, sufficient oxygen may be introduced to eliminate these undesirable effects without unduly interfering with nitrate and nitrite reduction.

Insofar as the first stage is concerned, the organic waste water influent provides the carbon source for the facultative bacteria in the recycled activated sludge in the first stage to effect denitrification of the nitrates and nitrites.

Insofar as the third stage is concerned, the denitrification capacity is provided by the respiratory activity of the sludge passing from the second stage to the third stage.

To operate the first and third stages under anoxic conditions, it may be necessary in certain cases to exclude air from these stages by substantially enclosing them.

It is known that biological processes are adversely affected by a decrease in temperature below about 30°C.

Applicants believe that unless the temperature drops materially below about 20°C, the reduced respiration rate in the first stage will be of little consequence in view of the concentration of facultative bacteria in the first stage from the recycled activated sludge, and the carbon source provided by the organic waste water influent.

However, if the temperature drops below about 15°C, the reduced respiration rate in the third stage may result in insufficient denitrification in the process of this invention.

In this regard, the enclosing of the first and third stages can assist in combatting heat loss. This can however only have a limited effect.

Therefore, to combat insufficient denitrification in the third stage as a result of a temperature drop, it may be necessary to increase the capacity of the third stage so that the denitrification rate will be sufficient under all conditions which will be encountered.

The capital costs involved in increasing the capacity of the third stage may however be excessive, particularly where seasonal ambient temperature variations would be high.

As an alternative or additional method of combatting insufficient denitrification in the third stage, a suitable carbon source may be provided in the third stage when required.

The process may therefore include the step of providing a suitable carbon source in the third stage to improve the respiration rate if it drops below that needed for maintaining a sufficient level of denitrification in the process.

By weighing up the capital costs involved in increasing the capacity of the third stage against the costs of periodically providing a carbon source in the third stage, a decision can be made in regard to the operation of the process of this invention in a particular environment.

The carbon source may be in the form of any suitable nitrogen-free carbon source. Thus, for example, it may be in the form of methanol.

Insofar as the second stage is concerned, while the ecology of autotrophic nitrifying bacteria is not yet fully understood, Applicants have found that activated sludge systems can be operated to give persistent and reliable nitrification of nitrogen compounds above about 10°C.

If the oxygen tension is sufficiently high, the nitrifying bacteria present in activated sludge will convert nitrogenous compounds into nitrates. Thus, ammonia will be converted to nitrites and nitrates, and nitrites will be converted to nitrates.

The limiting factor appears to be the conversion of ammonia to nitrites. Nitrites tend to be rapidly and readily converted to nitrates. During nitrification therefore, the resultant product will be in the form of nitrates.

The second stage of the process of this invention is therefore operated under aerobic conditions by aeration to provide biological oxidation of the dissolved nitrogenous compounds to nitrates.

The second stage may be aerated by any suitable means. Thus, for example, it may be aerated by means of surface aeration means or by submerged aeration means.

Surface aeration means may, for example, be in the form of aeration discs. Submerged aeration means may, for example, comprise blowing air, pure oxygen or a mixture of air and oxygen into the mixed liquor in the second stage.

Surface aeration has the disadvantage that it can tend to provide a cooling effect where the ambient temperature is low, and its application is limited by the depth of the liquid being aerated. Submerged aeration can tend to provide a beneficial heating effect as a result of the compression of air or oxygen which is then released below the level of the liquid being aerated. This should therefore be taken into consideration where the ambient temperature will tend to be a factor.

The dissolved oxygen concentration should be sufficiently high to maintain aerobic conditions. It should however not be too high since it can then have a detrimental effect on denitrification in the first and third stages as a result of excessive oxygen carry-over in the recycling of mixed liquor from the second stage to the first stage, and in the feeding of mixed liquor from the second stage to the third stage.

The dissolved oxygen concentration in the second stage may, for example, be between about 0.5 and about 4 mg/l. It may conveniently be between about 0.5 and about 2 mg/l. It should be controlled at the level of the lowest value which would still give good nitrification. This level may be higher in winter than in summer.

The dissolved oxygen concentration in the second stage may therefore be measured periodically, and the aeration means may then be adjusted appropriately. Alternatively, automatic control means may be used for measuring and controlling the dissolved oxygen concentration.

Insofar as the second stage is concerned, the solids retention time is important since it should be sufficiently long to prevent undue wash out of nitrifying organisms. This can be controlled by controlling the size of the second stage and/or the mixed liquor suspended solids concentration in the process.

The nitrifying organisms are temperature dependent. Using Downing's experimental results (Downing, A. L., Painter, H. A. and Knowles, G. — 'Nitrification in the activated sludge process' — Journal Proc. Inst. Sewage Purif. pt 2, P.130(1964)) on the relationship between temperature and growth rate for these micro-organisms, minimum solids retention times or sludge ages to ensure nitrification can be calculated as shown in FIG. 1 of the attached drawings.

The rate of recycling of mixed liquor from the second stage to the first stage may be controlled in relation to the influent feed rate and the concentration of nitrogenous compounds in the organic waste water influent, to obtain significant denitrification in the first stage.

The recycling rate may conveniently be controlled to obtain a reduction of nitrates and nitrites in the first stage, to such a level that the respiratory activity of the bacterial population in the third stage can be significant in relation to the nitrates passing from the second stage to the third stage.

The rate at which mixed liquor should be recycled from the second stage to the first stage depends upon the influent feed rate of organic waste water, the concentration of nitrogenous compounds in the influent, the amount of nitrates which can be reduced in the third stage and the retention time in the first stage.

The recycle rate of the mixed liquor may therefore conveniently be determined by calculating and estimating the amount of nitrates which can be reduced in the third stage. Thus the recycle rate may be controlled so that the level of nitrates in the second stage does not exceed that which can be reduced in the third stage.

If the recycle rate of mixed liquor is too low, the amount of nitrates passing from the second stage to the third stage will be in excess of that which can be reduced in the third stage, thereby giving rise to unsatisfactory nitrate levels in the effluent.

As the recycle rate of mixed liquor increases above the optimum value, the required process capacity will be increased to handle the increased flow, thereby reducing the economy and efficiency of the process.

The recycling rate may conveniently be at least about 2 : 1 by volume in relation to the influent feed rate. Thus, for example, it may vary between about 2 : 1 and about 10 : 1 by volume in relation to the influent feed rate.

The recycling of the active sludge may be controlled to ensure a suitable solids concentration in the various stages of the process and thus ensure the presence of a bacterial population which will be effective in the denitrification and nitrification stages of the process.

For maximum nitrification and denitrification, especially during colder months, a high mixed liquor suspended solids (MLSS) concentration is desirable. If the concentration is above the optimum, it will again influence the process capacity.

In an embodiment of the invention, the recycling of active sludge may be controlled to provide an MLSS concentration of at least about 2 000 mg/l.

The process may include the step of recycling a minor portion of active sludge from the solids separation stage to the second stage if the level of the bacterial population in the second stage is too low. This should however only be required in exceptional circumstances.

Applicants have found that in processes where only nitrification is carried out, the pH value sometimes drops to low levels. This affects nitrification adversely and the pH must therefore be adjusted.

Applicants have found that in the process of this invention, where both denitrification and nitrification are carried out, the pH does not tend to drop. In fact, in experiments conducted with unbuffered waters, an increase in the pH value has been noted.

However, if the pH of the influent is too low, it is advisable to raise the pH as a pre-treatment step to provide optimum nitrification. The pH should conveniently be raised to at least about pH 6.2. The optimum pH value is about 8.2.

The process may include the step of providing stirring means in the first and third stages to provide gentle stirring for mixing purposes only.

The solids separation stage may be of any suitable type. Thus, for example, it may be in the form of a clarifier stage, a flotation stage or a sedimentation stage.

The process may include the further step of interposing a fourth stage in the form of an aeration stage, between the third stage and the solids separation stage. The purpose of the fourth stage is to drive off gas bubbles which may hinder solids separation, and for stabilising the sludge to facilitate solids separation. The fourth stage may operate in the form of a nitrification stage to nitrify ammonia which may be released in the third stage.

The process may be operated to remove phosphates where the organic waste water contains phosphates. This aspect is described later. Alternatively, or additionally, the process may include the further step of treating the organic waste water with suitable chemicals in a phosphate removal step, to remove phosphates.

This phosphate removal step may be carried out at any convenient stage in the process of this invention.

Any of the chemicals which are known to be suitable for phosphate removal, and which will not be detrimental to the nitrogen removal process, may be used. Thus, for example, chemicals such as alum, aluminate or iron slats may be used.

The invention further extends to apparatus for use in carrying out the process as described, and comprising a first stage in the form of a denitrification stage for receiving organic waste water containing nitrogenous compounds, a second stage in the form of a nitrification stage, a third stage in the form of a denitrification stage, a solids separation stage for providing a clarified effluent and an active sludge, mixed liquor recycling means for recycling mixed liquor from the second stage to the first stage, and sludge recycling means for recycling at least portion of the active sludge provided by the solids separation stage, to the first stage.

The mixed liquor recycling means may be in the form of pump means which is capable of recycling the mixed liquor at a required rate for the carrying out of the process.

The sludge recycling means may be in the form of pump means capable of recycling any active sludge at a desired rate for carrying out the process.

The apparatus may include gravity feed means to feed mixed liquor under the action of gravity from the first stage to the second stage, from the second stage to the third stage and from the third stage to the solids separation stage.

The feed means from the first stage to the second stage may be arranged to take up mixed liquor overflow from the first stage and feed it into a submerged region of the second stage. The feed means between the second stage and the third stage may operate in the same manner.

The mixed liquor recycling means from the second stage to the first stage, may be arranged to draw mixed liquor from the second stage and recycle it into the first stage, so that any short-circuiting in the first stage and in the second stage is minimised.

Since the second stage is in the form of a nitrification stage, the apparatus includes aeration means for aerating the second stage.

The aeration means may be in the form of surface aeration means or in the form of submerged aeration means.

Where the aeration means is in the form of surface aeration means, it may, for example, be in the form of one or more aeration discs which are adapted to be rotatably driven to carry entrained air into the body of mixed liquor in the second stage.

Where the aeration means is in the form of submerged aeration means it may, for example, be in the form of air or oxygen supply means to lead compressed air or oxygen into the second stage and release the air or oxygen in a submerged position.

The apparatus may include stirrer means in the first and third stages to provide gentle stirring for the purposes of mixing.

To assist in operating the first and third stages under anoxic conditions, the apparatus may in certain cases, include cover means for covering the first and third stages to reduce air contact with these stages.

The cover means may be of any suitable type. In an embodiment of the invention, the cover means may be in the form of covers of foamed or expanded synthetic plastic material.

Where ambient temperatures are low, cover means may also be provided on the second stage to assist in combatting heat loss from the apparatus.

The apparatus may further include carbon source feed means for feeding a suitable nitrogen-free carbon source to the third stage when required.

The apparatus may further include a fourth stage in the form of an aeration stage which is interposed between the third stage and the solids separation stage, for driving off gas bubbles which may hinder solids separation in the solids separation stage and for stabilising the sludge to facilitate solids separation.

The fourth stage may operate in the form of a nitrification stage to nitrify ammonia which may be released in the third stage during operation of the process.

Where the apparatus includes a fourth stage, the feed means as hereinbefore described between the third stage and the solids separation stage, will be replaced by feed means from the third stage to the fourth stage, and feed means from the fourth stage to the solids separation stage. This feed means may again be in the form of gravity feed means as hereinbefore described.

The solids separation stage may be of any suitable type. Thus, for example, it may be in the form of a clarifying stage, a flotation stage or a sedimentation stage.

The first to fourth stages of the apparatus may be in the form of any suitable types of vessels, depending upon the capacity for which the apparatus is designed, the economic considerations applicable to the construction of the apparatus, whether or not provision must be made for increasing the capacity of the apparatus, and the like.

Thus, for example, if the apparatus were to be designed for handling up to about 25 000 $m^3$ of organic waste water influent per day, the second and fourth stages could conveniently be in the form of endless annular channels, with the denitrification stages located within the area bounded by the endless annular channels.

If provision for expansion was required, then an area could be set aside to allow further apparatus of the same capacity to be constructed.

However, if the available surface area is the limiting factor, and excavation presents no major difficulties, the various stages could be in the form of vessels which are recessed into the ground and located adjacent to each other. In this arrangement, the depth of the various vessels could be up to 30 feet or more thereby drastically reducing the surface area required for the apparatus.

The stages of the apparatus may be constructed of any desired material. They may conveniently be constructed out of concrete, out of prefabricated concrete panels, or the like.

In applications where the apparatus would have a capacity in excess of about 20,000 m$^3$ per day of influent organic waste water, the economic considerations would normally point to construction of the plant by excavating up to depths of about 30 feet or more and constructing the four stages of the apparatus adjacent to each other in the excavated zone.

Since it is envisaged that the process and apparatus of this invention could be used in conjunction with physical-chemical units for water reclamation, equalization of flow may have to be provided for.

This could be provided for by having the first stage of a sufficient size. The first stage would then serve the purpose of equalization as well as denitrification. The mixed liquor can thus be fed from the first stage to the second stage at a constant rate. Furthermore, the recycling of nitrates from the second stage to the first stage as a result of the recycling of mixed liquor, will tend to combat septicity in the first stage.

While this invention can have application in regard to the treatment of nitrogen containing organic waste waters in general, it has particular application in regard to the treatment of waste water in the form of sewage. The sewage may be in the form of raw sewage or settled sewage.

Embodiments of the invention are now described by way of example with reference to the accompanying drawings, and with reference to various experiments which were conducted with some of the apparatus as illustrated in the drawings.

Figure 1:
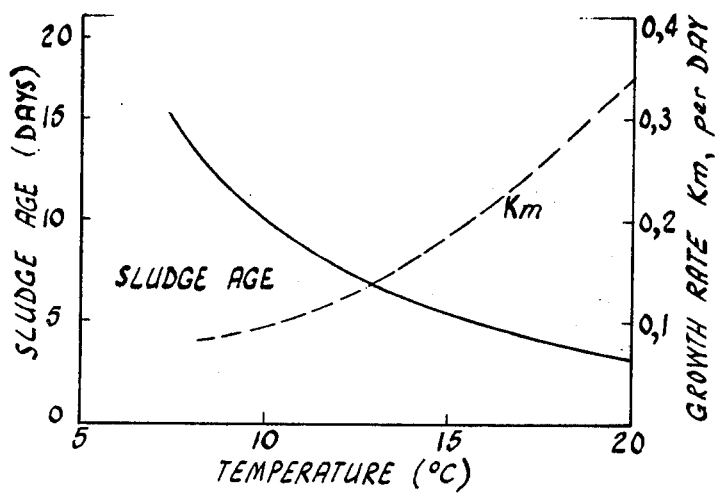
FIG. 1 shows a graph of Downing's experimental results as hereinbefore described, for determining minimum solids retention times or sludge ages to ensure nitrification.
Figure 2:
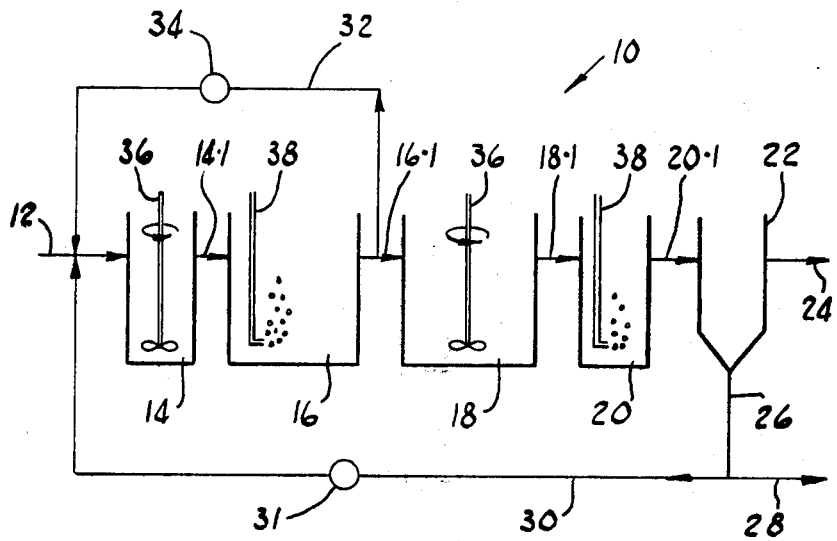
FIG. 2 shows a diagrammatic flow sheet of the process and apparatus of this invention, for the treatment of organic waste water in the form of settled sewage, to remove nitrogenous compounds from the sewage.
Figure 6:
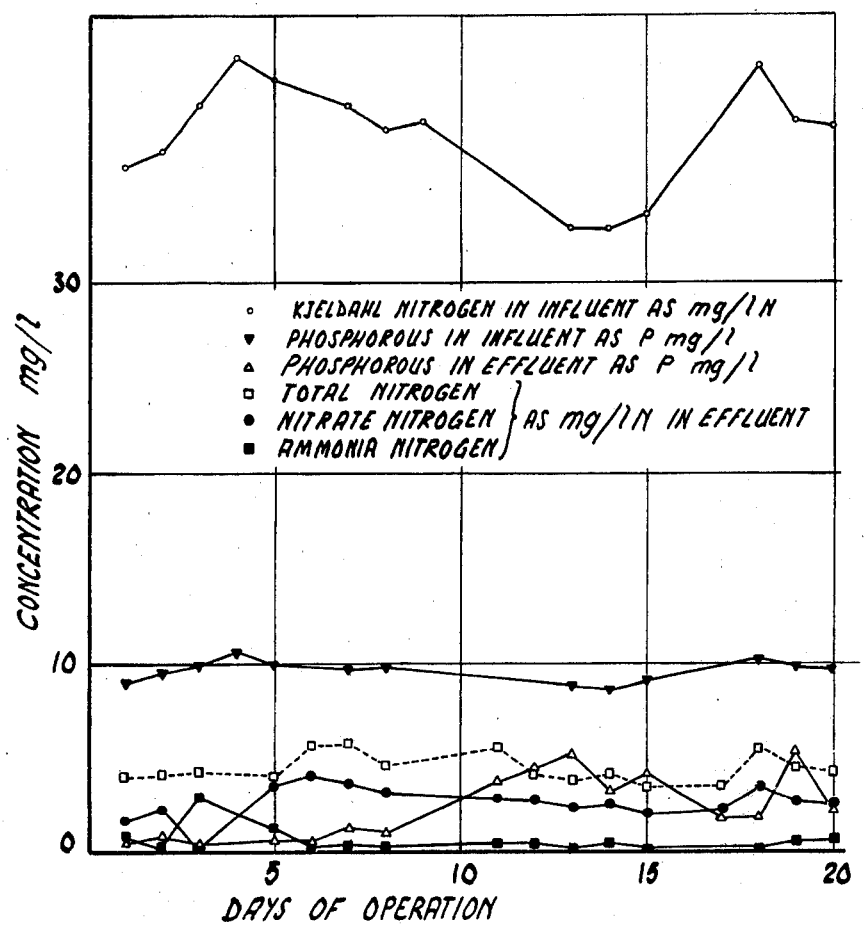

FIG. 6 sets out graphically the results obtained in relation to nitrogen and phosphorous when the apparatus of FIG. 2 of the drawings was operated on a pilot plant scale over a period of twenty days; and FIG. 7 sets out graphically the chemical oxygen demand in milligrams per liter (C.O.D.) and the phosphates as phosphorous in milligrams per liter in the effluent when the pilot plant was operated continuously for a period of six weeks, to obtain phosphate removal.

With reference to FIG. 2 of the drawings, there is shown a diagrammatic flow sheet illustrating the process and apparatus of this invention, adapted for treating organic waste water in the form of settled sewage, for the removal of nitrogenous compounds dissolved and/or suspended therein.

The apparatus has feed means 12 for feeding settled sewage to the apparatus 10.

Raw sewage would normally be subjected to the usual screening and preliminary sedimentation procedures, whereafter the settled sewage would be allowed to flow under the action of gravity into the apparatus 10 via the feed means 12.

The apparatus 10 comprises a first stage 14 in the form of a biological denitrification stage, a second stage 16 in the form of a biological nitrification stage, a third stage 18 in the form of a biological denitrification stage, a fourth stage 20 in the form of an aeration stage, and a solids separation stage 22 for providing a clarified effluent leaving the apparatus 10 at 24 and an active sludge leaving the solids separation stage 22 at 26.

The apparatus 10 includes a waste conduit 28 for leading waste sludge out of the apparatus 10 to waste, and sludge recycling means 30 with pump means 31 for recycling portion of the active sludge to the first stage 14.

The apparatus 10 further includes a mixed liquor recycling conduit 32 and recycling pump means 34 for recycling mixed liquor from the second stage 16 to the first stage 14.

The apparatus 10 further includes gravity feed means 14.1, 16.1, 18.1, and 20.1 for feeding the mixed liquor under the action of gravity from the first stage to the second stage, from the second stage to the third stage, from the third stage to the fourth stage, and from the fourth stage to the solids separation stage 22 respectively.

The feed means from each stage is arranged to feed the overflow of mixed liquor from the preceding stage into the succeeding stage, so that the mixed liquor so fed will gravitate towards the bottom of the succeeding stage.

The mixed liquor recycling conduit 32 is arranged to take up mixed liquor from the second stage 16 adjacent to the feed means 16.1 thereby combatting any short-circuiting in the second stage 16. This mixed liquor is recycled into the first stage 14 in the vicinity of the feed means 12, thereby again combatting any short-circuiting between the recycled mixed liquor, and the mixed liquor leaving the first stage 14 through the feed means 14.1.

Stirring means 36 is provided in the first and third stages 14 and 18 to provide gentle stirring for the purposes of mixing only.

Insofar as the first and third stages 14 and 18 are concerned, these are operated under anoxic conditions.

Insofar as the second and fourth stages 16 and 20 are concerned, these are aerobic stages which are operated under aerobic conditions to allow nitrification to take place in the second stage 16, and in the fourth stage 20 insofar as any ammonia is concerned which may be released in the third stage 18. The fourth stage 20 further serves to drive off gas bubbles which may hinder solids separation and to stabilize the sludge to facilitate solids separation.

Insofar as the second stage 16 is concerned, the aeration is controlled so that the dissolved oxygen concentration is sufficiently high for nitrification to take place, but is not too high to provide an undue dissolved oxygen carryover from the second stage 16 to the third stage 18 via the feed means 16.1, and from the second stage 16 via the mixed liquor recycling conduit 32 to the first stage 14.

In experiments which have been conducted, it was found that aeration could conveniently be controlled to provide a dissolved oxygen concentration in the second stage 16 of about 2 mg/l to about 0.5 mg/l.

Figure 3:
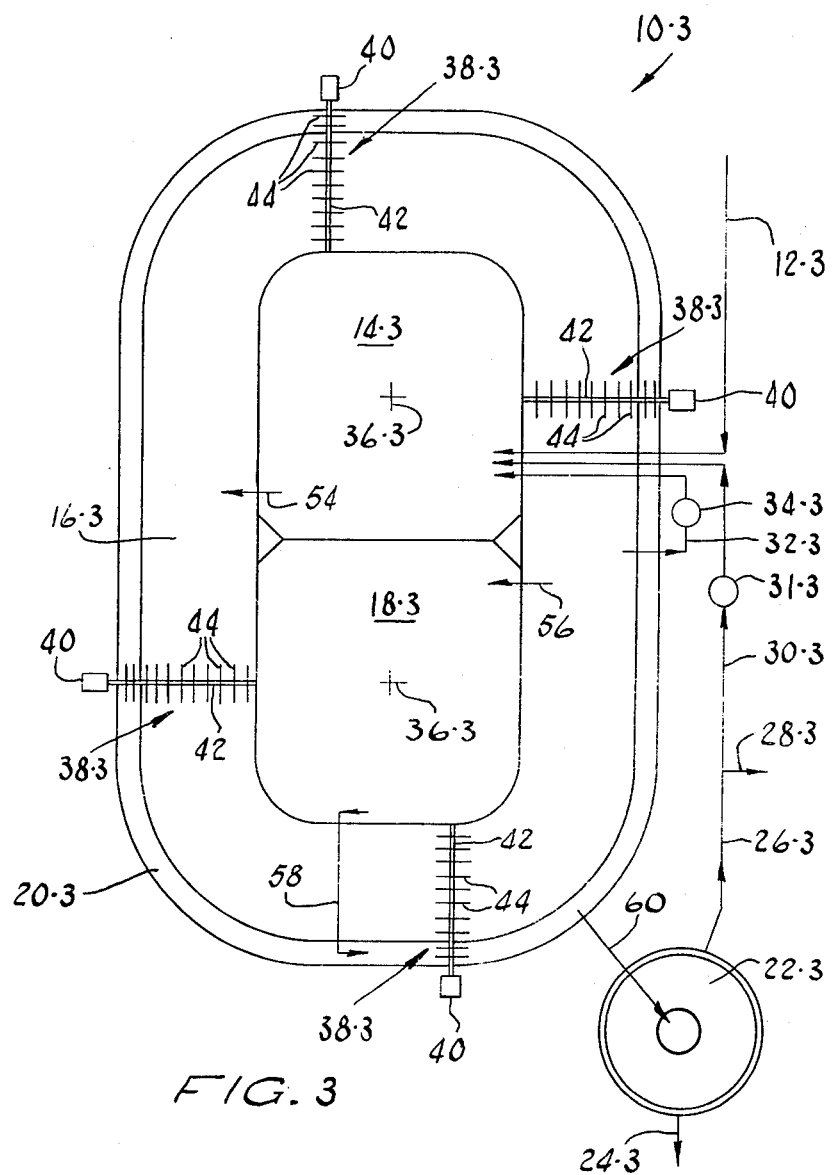
FIG. 3 shows a diagrammatic plan view of one embodiment of the apparatus for carrying out the process of this invention.

With reference to FIG. 3 of the drawings, reference numeral 10.3 refers generally to one embodiment of an apparatus arrangement for carrying out the process of this invention.

The form of the apparatus as illustrated diagrammatically in FIG. 3 of the drawings, would tend to be applied where the surface area occupied by the apparatus 10.3 is not critical and where the required capacity would be less than about 25,000 m³ of organic waste water per day.

The apparatus 10.3 comprises feed means 12.3 for feeding organic waste water into the apparatus 10.3.

The apparatus 10.3 further comprises a first stage 14.3 in the form of a denitrification stage, a second stage 16.3 in the form of a nitrification stage, a third stage 18.3 in the form of a denitrification stage, a fourth stage 20.3 in the form of an aeration stage, and a solids separation stage 22.3 for providing a clarified effluent leaving the apparatus 10.3 at 24.3, and an active sludge leaving the solids separation stage 22.3 at 26.3.

The apparatus 10.3 includes a waste coonduit 28.3 for leading waste sludge out of the apparatus 10.3, and sludge recycling means 30.3 with pump means 31.3 for recycling at least portion of the active sludge to the first stage 14.3. The apparatus 10.3 further includes a mixed liquor recycling conduit 32.3 and recycling pump means 34.3 for recycling mixed liquor from the second stage 16.3 to the first stage 14.3.

The apparatus 10 further includes feed means 54, 56, 58 and 60 for feeding the mixed liquor successively through the stages and to the solids separation stage respectively.

Stirring means 36.3 is provided in the first and third stages 14.3 and 18.3 to provide gentle stirring for the purpose of mixing only.

The first and third stages 14.3 and 18.3 are anoxic stages wherein nitrites and nitrates are reduced thereby leading to nitrogen gas, nitrous oxide and other minor forms of nitrogenous gas being evolved.

If the dissolved oxygen concentration in the first and third stages 14.3 and 18.3. is being adversely affected by contact with air, these stages may be covered with suitable covering means. The covering means may conveniently be in the form of covers of expanded or foamed synthetic plastic material.

Insofar as the second and fourth stages 16.3 and 20.3 are concerned, these are aerobic stages. They therefore include aeration means 38.3 for aerating these two stages.

The second and fourth stages 16.3 and 20.3 are in the form of endless annular channels which are concentrically arranged, and the first and third stages 14.3 and 18.3. are provided within these channels.

Since the stages 16.3 and 20.3 would usually tend to be constructed so that they are shallow enough for surface aeration to be effective, the aeration means 38.3 is shown to be in the form of surface aeration means.

In the embodiment illustrated in FIG. 3 of the drawings, the aeration means 38.3 comprises four diametrically opposed aeration systems.

Each aeration system comprises a motor 40 for rotatably driving a rotatably mounted shaft 42. Each shaft 42 has a plurality of aeration discs 44 mounted thereon.

Each aeration disc 44 is provided with a multiplicity of apertures or nodules for entraining air and carrying entrained air into the mixed liquor in the stages 16.3 and 20.3 during rotation of the shafts 42.

The aeration means 38.3 therefore serves to aerate the mixed liquor as well as displace the mixed liquor along the stages 16.3 and 20.3.

The apparatus 10.3 may include automatic control means (not shown) to test the dissolved oxygen concentration in the stages 16.3 and 20.3, and control the aeration means 38.3 accordingly so that the desired levels are maintained.

Figure 4:
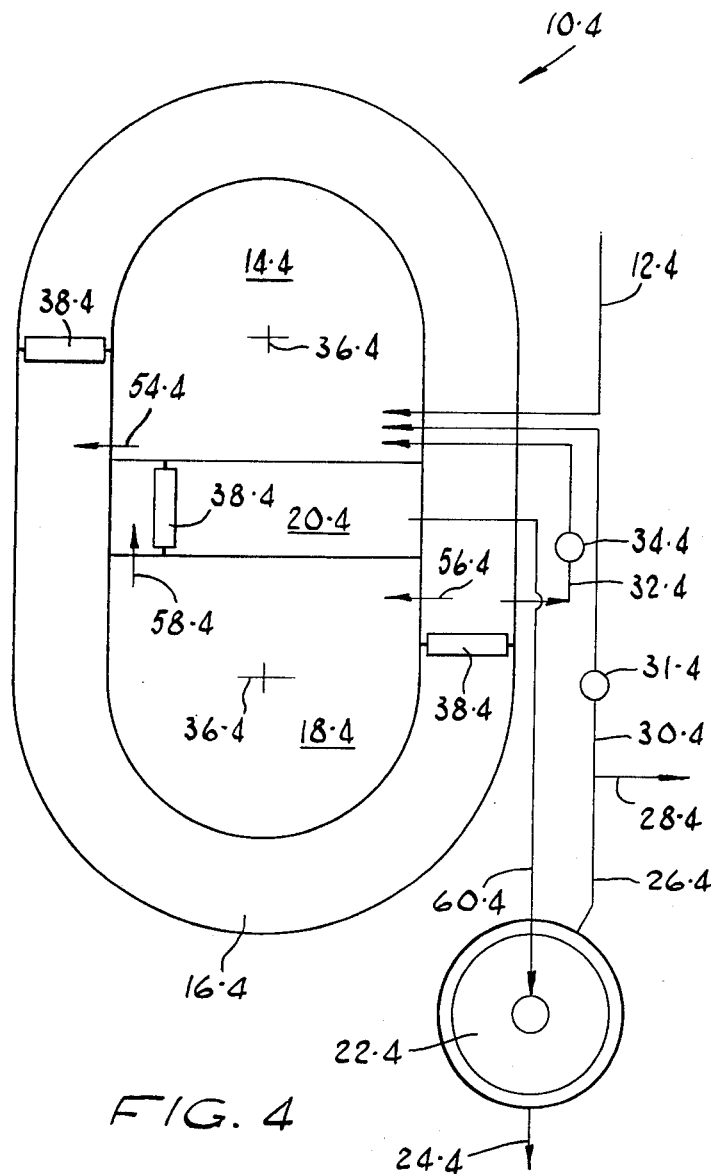
FIG. 4 shows a diagrammatic plan view of an alternative embodiment of the apparatus for carrying out the process of this invention.

With reference to FIG. 4 of the drawings, reference numeral 10.4 refers generally to a further embodiment of an apparatus arrangement for carrying out the process of this invention.

The form of the apparatus 10.4 as illustrated diagrammatically in FIG. 4 of the drawings, would tend to be applied in the same circumstances as in the case of the apparatus arrangement as illustrated in FIG. 3 of the drawings.

The apparatus 10.4 is generally similar to the apparatus 10.3, and comprises feed means 12.4 for feeding organic waste water into the apparatus 10.4.

The apparatus 10.4 further comprises a first stage 14.4 in the form of a denitrification stage, a second stage 16.4 in the form of a nitrification stage, a third stage 18.4 in the form of a denitrification stage, a fourth stage 20.4 in the form of an aeration stage, and a solids separation stage 22.4 for providing a clarified effluent leaving the apparatus 10.4 at 24.4, and an active sludge leaving the solids separation stage 22.4 at 26.4.

The apparatus 10.4 again includes a waste conduit 28.4 for leading waste sludge out of the apparatus 10.4, and sludge recycling means 30.4 with pump means 31.4 for recycling at least portion of the active sludge to the first stage 14.4.

The apparatus 10.4 further includes a mixed liquor recycling conduit 32.4 and recycling pump means 34.4 for recycling mixed liquor from the second stage 16.4 to the first stage 14.4.

The apparatus 10.4 again includes feed means 54.5, 56.4, 58.4 and 60.4 for feeding mixed liquor under the action of gravity through the various stages of the apparatus.

The first and third stages 14.4 and 18.4 again include stirring means 36.4 to provide gentle stirring for the purposes of mixing.

The second and fourth stages 16.4 and 20.4 are again aerobic stages, and include aeration means 38.4 for aerating these two stages. The aeration means is again in the form of surface aeration means and comprises rotatably mounted aeration rotors, which are adapted to be rotatably driven to aerate the mixed liquor and to convey the mixed liquor along the stages 16.4 and 20.4.

Contrary to the apparatus arrangement as illustrated in FIG. 3, only the second stage 16.4 is in the form of an endless annular channel.

Figure 5:
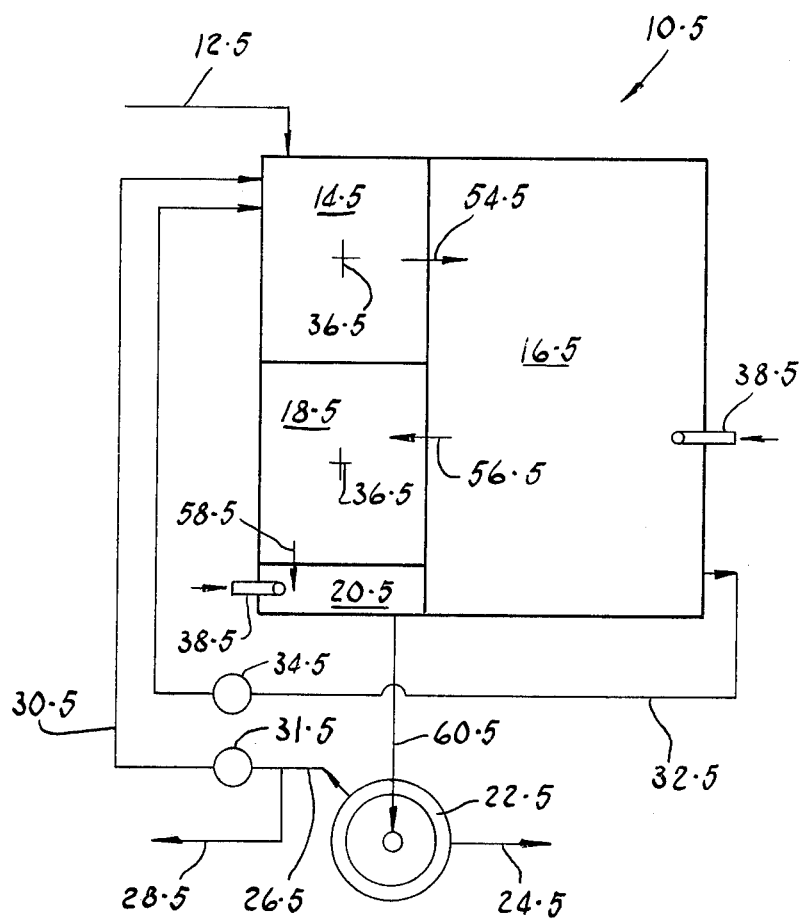
FIG. 5 shows a diagrammatic plan view of a further alternative embodiment of the apparatus for carrying out the process of this invention.

With reference to FIG. 5 of the drawings, reference numeral 10.5 refers generally to a further embodiment of an apparatus arrangement for carrying out the process of this invention.

The form of the apparatus 10.5 as illustrated diagrammatically in FIG. 5 of the drawings, would tend to be applied where the surface area occupied by the apparatus is of importance, or where submerged aeration would tend to be applied.

The apparatus 10.5 again includes feed means 12.5 for feeding organic waste water into the apparatus.

The apparatus 10.5 further comprises a first stage 14.5 in the form of a denitrification stage, a second stage 16.5 in the form of a nitrification stage, a third stage 18.5 in the form of a denitrification stage, a fourth stage 20.5 in the form of an aeration stage, and a solids separation stage 22.5 for providing a clarified effluent leaving the apparatus 10.5 at 24.5, and an active sludge leaving the solids separation stage 22.5 at 26.5.

The apparatus 10.5 again includes a waste conduit 28.5 for leading waste sludge out of the apparatus 10.5, and sludge recycling means 30.5 with pump means 31.5 for recycling at least portion of the active sludge to the first stage 14.5.

The apparatus 10.5 again includes a mixed liquor recycling conduit 32.5 and recycling pump means 34.5 for recycling mixed liquor from the second stage 16.5 to the first stage 14.5.

The apparatus 10.5 further includes feed means 54.5, 56.5, 58.5 and 60.5 to feed mixed liquor through the various stages of the apparatus 10.5.

The feed means may again be in the form of gravity feed means. However, if the first stage is also intended to serve as a flow equalization stage, then the feed means 54.5 may be in the form of pump means.

Stirring means 36.5 is again provided in the first and third stages 14.5 and 18.5.

The second and fourth stages are again in the form of aerobic stages and include aeration means 38.5 for aerating these two stages.

In this embodiment of the apparatus, if the depth of the various stages is too great for surface aeration, then submerged aeration would be used. The aeration means 38.5 would therefore be in the form of aeration conduits to lead compressed air or pure oxygen into submerged regions of the stages 16.5 and 20.5.

The apparatus 10.5 would tend to be applied particularly in the case where the required sewage influent capacity is more than about 20,000 m³ per day. If the capacity to be handled by the apparatus is far in excess of this amount, the apparatus may comprise repeating modules with each module corresponding to the apparatus 10.5.

For the construction of the apparatus 10.5, a hole could be excavated up to the required depth. This could be up to about 30 feet or more and the various stages 14.5, 16.5, 18.5, and 20.5 constructed in the excavated hole.

Insofar as the apparatus 10.3, 10.4 and 10.5 are concerned, the drawings have been drawn generally to scale for the case where the retention times based on the average dry weather flow rates would be about 4 hours in the first stage, about 4 hours in the third stage, about 15 hours in the second stage and about 2 hours in the fourth stage. These retention times are based on the average dry weather flow rate and do not take into account the recycle rates of mixed liquor and of activated sludge.

It will be appreciated that the arrangement as illustrated in FIG. 5 of the drawings, is an economical arrangement. It can be rearranged and the shapes of the various stages can be altered as desired.

A number of experiments were then conducted on a laboratory scale with the apparatus arrangement as illustrated in FIG. 2 of the drawings. The average of the results of these various experiments are set out in Table I below.

The experiments were conducted at operating temperatures between about 20°C and 23°C, and the influent flow rate of settled sewage was 1 liter per hour. The solids separation stage was in the form of a clarifier and is indicated as such in Table I.

The retention times which were used during the experiments in the various stages, were as follows:
First stage 14 — about 2 hours;
Second stage 16 – about 6 hours;
Third stage 18 – about 6 hours; and
Fourth stage 20 – about 2 hours.

The retention times indicates above, are not the true retention times since they will vary if the recycling of mixed liquor from the first stage to the second, and the recycling of active sludge is taken into account. Thus, for example, where the recycle ratio by volume in relation to the feed rate of influent sewage is 2 : 1 insofar as the recycle rate of mixed liquor from the second stage to the first stage is concerned, and is 1 : 1 in relation to the recycle rate of active sludge from the clarifying stage 22 to the first stage 14 is concerned, the actual retention time in the first stage 14, was about 30 minutes. Similarly, the actual retention times in the other stages were about 1,5 hours in the second stage, about 3 hours in the third stage and about 1 hour in the fourth stage.

In table I below, the first column indicates the active sludge recycle ratio in relation to the influent feed rate of settled sewage by volume, whereas the second column indicates the mixed liquor (M.L.) recycle ratio from the second stage 16 to the first stage 14 in relation to the influent feed rate of settled sewage by volume.

In Table I below, the chemical oxygen demand (C.O.D.) is indicated in milligrams per liter in the influent and the effluent. Furthermore, by "T.K.N." is meant "Total Kjeldahl Nitrogen" in milligrams per liter, and by NO₃–N is meant the nitrate concentration as nitrogen in milligrams per liter.

TABLE I

| Recycle Sludge from clarifier | M.L. from second stage | Date | COD (mg/l) Feed | COD Effluent | TKN (mg/l) Feed | TKN Stage 1 | Stage 2 | Stage 3 | Stage 4 | $NO_3$—N (mg/l) Stage 1 | Stage 2 | Stage 3 | Stage 4 | Per cent Nitrogen Removal |
|---|---|---|---|---|---|---|---|---|---|---|---|---|---|---|
| 1:1 | 2:1 | 9/2 | 310 | 30 | 58 | 15,6 | 2,6 | — | 2,2 | 1,6 | 17,0 | 3,0 | 8,2 | 82,4 |
|  |  | 13/2 | 470 | 40 | 86 | 18,6 | 2,2 | 3,6 | 2,0 | 4,8 | >20 | 10,0 | 15,4 | 81,5 |
|  |  | 14/2 | 460 | 38 | 89 | 18,4 | 1,8 | 3,0 | 1,6 | 0,8 | 23,5 | 7,4 | 10,8 | 86,0 |
|  |  | 16/2 | 500 | 40 | 75 | 17,4 | 1,6 | 3,0 | 1,4 | 0,6 | 20,0 | 3,0 | 6,6 | 89,5 |
|  |  | 17/2 | 560 | 42 | 90 | 11,0 | 2,4 | 4,0 | 1,4 | 2,4 | 15,2 | 1,0 | 4,6 | 93,4 |
|  |  | 18/2 | 340 | 42 | 81 | 13,0 | 1,6 | 3,4 | 1,6 | 0,8 | 15,0 | 0,8 | 3,4 | 93,8 |
| 1:1 | 4:1 | 19/2 | 280 | 30 | 71 | 10,2 | 1,8 | 2,4 | 1,8 | 1,0 | 12,2 | 0,8 | 2,8 | 93,2 |
|  |  | 20/2 | 270 | 34 | 68 | 9,8 | 1,8 | 2,4 | 1,8 | 2,2 | 13,2 | 1,0 | 2,8 | 93,2 |

It will be noted from the experimental results obtained as set out in Table I, that virtual complete nitrification was achieved in the second and fourth stages. This can be seen from the low values of the Total Kjeldahl Nitrogen. It will further be noted that virtual complete denitrification was achieved in the first and third stages as can be seen from the low nitrate values. Total nitrogen removals of over 93% were obtained.

The retention times which were used in the experiments which were conducted, were selected rather arbitrarily. Applicants believe that more suitable retention times can be used. This will be illustrated hereinafter with reference to a design example.

In conducting the various experiments as indicated above, the operation of the process was controlled by monitoring the nitrates in each of the stages, and the dissolved oxygen concentration in the second and fourth stages. Applicants further found that a check on the ammonia leaving the apparatus was useful. This is particularly the case where breakpoint chlorination is intended to be applied to the clarified effluent leaving the apparatus.

As stated previously, the addition of limited amounts of methanol or other carbon sources to the third stage, will tend to boost the activity of this stage during periods of low activity. This will therefore allow a reduction of the size of the third stage. In this connection it should be noted that excessive retention times in the third stage may lead to a rise in the ammonia content, thereby combatting the efficiency of the process.

A number of further experiments werre conducted on a pilot plant scale with the apparatus arrangement as illustrated in FIG. 2 of the drawings.

The pilot plant was operated with a constant feed of 100 m³ per day of settled sewage which was obtained from the influent of a municipal sewage treatment plant.

The settled sewage was drawn off at a constant rate such that daily fluctuations in the pollutant concentration of the sewage was taken into account but not the daily flow variation.

The average daily chemical oxygen demand (C.O.D.) of the incoming settled sewage varied between 300 mg/l during rainy spells and 700 mg/l during prolonged dry periods. The Total Kjeldahl Nitrogen entering the pilot plant varied between 30 and 40 mg/l as nitrogen. The plant was operated using 2 hours retention, based on the settled sewage flow rate, for the first stage, 6 hours retention for the second stage, 4 hours retention for the third stage, and 1 hour retention in the fourth stage.

The sludge return flow was 1 : 1 by volume in relation to the settled sewage flow rate, and the mixed liquor recycle rate from the second stage to the first stage was 3 : 1 by volume in relation to the flow rate of settled sewage.

Effluent samples were collected every 2 hours by means of an automatic sampler. The results plotted in FIG. 6 of the drawings, are the average values of the effluent parameters taken over a few weeks of continuous running.

In FIG. 6 of the drawings, the ordinate of the graph represents the concentration in mg/l, whereas the abscissa represents the days of operation.

Furthermore, the different symbols used to indicate the different values on the graph, have the following means:

a. Plain circle — Kjeldahl nitrogen in influent as mg/l nitrogen.

b. Inverted blackened triangle — Phosphorous in influent as P. (mg/l).

c. Plain square — Total nitrogen in effluent as mg/l nitrogen.

d. Blackened circle — Nitrate nitrogen in effluent as mg/l nitrogen.

e. Blackened square — Ammonia nitrogen in effluent as mg/l nitrogen.

f. Plain non-inverted triangle — Phosphorous in effluent as P. (mg/l).

From the results shown in FIG. 6 of the drawings, it can be seen that the removal of nitrogen was substantial with total nitrogen including all forms of nitrogen, being between about 4 and 5 mg/l as nitrogen in the effluent:

It was also observed that the phosphates in the effluent were quite low. During the first half of the run, the phosphates were found to be around or below 1 mg/l as phosphorous. Thereafter the phosphates in the effluent steadily climbed to average 3 to 4 mg/l in the effluent. It was observed during this time that the mixed liquor suspended solids concentration was rising to levels of about 5,000 mg/l and sludge was accumulating in the clarifier. No sludge was wasted during this period.

Since no sludge was wasted during the period of the experiments as indicated above, precipitated phosphates remained in the sludge and thus remained in the system except for that portion which left the system in the clarified effluent.

In view of the reasonably low levels of phosphates in the clarified effluent, the process was adapted to obtain improved phosphate removals.

The invention therefore extends to the process as hereinbefore described, which includes the fourth stage comprising an aeration stage, and which includes the steps of, where the organic waste water contains phosphates, aerating the fourth stage to maintain a sufficient dissolved oxygen concentration in the fourth stage to obtain phosphate precipitation, and of wasting active sludge from the solids separation stage to remove phosphates from the organic waste water.

The fourth stage may be aerated to maintain a dissolved oxygen concentration of at least about 3 mg/l in the fourth stage. It may conveniently be aerated to maintain a dissolved oxygen concentration of at least about 4 mg/l in the fourth stage.

The active sludge may be wasted regularly to obtain phosphate removal. If desired, it may be wasted continuously.

The process may include the step of controlling the rate of recycle of active sludge from the solids separation stage to limit the residence time of the sludge in the solids separation stage and thus the development of carbon dioxide in the solids separation stage.

As the sludge residence time in the solids separation stage increases, carbon dioxide development will increase. This appears to lead to precipitates phosphates dissolving in the clarified effluent, thereby increasing the phosphate concentration in the clarified effluent.

The recycle rate of sludge should therefore be controlled to limit the phosphate concentration in the clarified effluent to levels which are possible and acceptable.

Applicants have found that if the sludge recycle rate is between about one and two times the average dry weather influent flow rate by volume, the phosphate concentration in the clarified effluent can generally be maintained below acceptable levels.

The proocess may include the further step of subjecting the sludge from the solids separation stage, to a sludge treatment process to provide a waste stream containing phosphates.

Such a waste stream containing phosphates would tend to be relatively small and concentrated. It could therefore be wasted on land, or could be treated for phosphate removal by any suitable conventional means prior to returning it to the process. It could therefore, for example, be treated with lime or any other suitable phosphate precipitant, the precipitated phosphates can then be removed and the treated stream can then be returned to the process.

Such treatment with lime, for example, would tend to be cheaper than treatment of the organic waste water with lime in view of the difference in relative volumes and concentrations of phosphates.

Lime treatment can provide the further advantage that it raises the pH of the treated stream. Thus when the treated stream is returned to the process, the increase in pH can be beneficial to nitrification and denitrification.

The sludge treatment process may be applied to the sludge which is recycled, to the sludge which is wasted, or to both.

Where it is applied to the sludge which is recycled, the sludge treatment process may comprise passing the sludge through an anaerobic basin before returning the sludge to the first stage.

The anaerobic basin may be of any suitable known type. Thus, for example, it may be in the form of a thickening tank where solids-liquid separation occurs and phosphates would go into solution.

Where the sludge treatment process is applied to wasted sludge, it may comprise such known processes as anaerobic or aerobic digestion, heat treatment, or dewatering prior to incineration.

To illustrate this application of the invention to phosphate removal, reference is now made, by way of example, to a number of further experiments which were conducted. These further experiments corresponded to those which were conducted and yielded the results as illustrated in FIG. 6 of the drawings, except that the active sludge was wasted regularly, aeration of the fourth stage was done more vigorously to maintain a dissolved oxygen concentration of about 4 mg/l in the fourth stage, and sludge was prevented from accumulating in the solids separation stage.

These experiments resulted in the effluent phosphate values as plotted in the graph comprising FIG. 7 of the drawings.

In FIG. 7 of the drawings the abscissa represents the days of operation, the ordinate for the upper part of the graph represents the C.O.D. (Chemical Oxygen Demand) in mg/l in the effluent and the ordinate for the lower part of the graph represents the concentration of phosphates as P in mg/l in the effluent.

During the first phase of the experiment, mechanical troubles were experienced with the sludge return pump. This resulted in higher values of the effluent phosphate concentration during this time. The influent phosphate concentration was of the order of about 12 mg/l and the removal efficiency was therefore in excess of 90%.

In the graph comprising FIG. 7 of the drawings, the average of the phosphate concentrations as phosphorous in the effluent is indicated by means of a dotted line, and was 0.7 mg/l. The average of the C.O.D. values in the effluent is further indicated by a dotted line, and was 39.4 mg/l.

From experiments conducted by the Applicants in connection with this invention, they have found that nitrate removal in the first stage in accordance with the process of this invention is related to the retention time in the first stage. It appears that there should be a certain minimum retention time based on the average dry weather flow rate of the influent, in the first stage.

If the retention time is below the minimum, then the nitrate removal will tend to decrease as the recycle rate of mixed liquor from the second stage to the first stage is increased. Applicants believe that this phenomena may be related to the dilution of the C.O.D. content below a minimum in the first stage as the recycle rate of mixed liquor is increased. This appears to be supported by the fact that the minimum required retention time is affected by temperature so that the minimum is reduced as the temperature increases.

If the retention time in the first stage is above the minimum, then an increased recycle rate of mixed liquor from the second stage to the first stage, will lead to an increase in nitrate removal in the first stage.

The first stage should therefore be designed to provide a retention time which is above the minimum.

This could, for example, be done in either of the following two ways.

The first way would be to increase the capacity of the first stage in separate stages in a pilot plant apparatus, and measure the nitrate removal in the first stage. The capacity of the first stage can thus be increased until such time as an increase in the recycle rate of mixed liquor from the second stage to the first stage, gives rise to an increase in overall nitrate removal in the first stage.

The second way would be to provide a plurality of separate basins, and to mix a volume of recycled active sludge with a volume of influent organic waste water in relation to the influent flow rates and active sludge recycle rates to be used in the process, in each of the basins. Thereafter, separate increasing volumes of recycled mixed liquor in relation to the mixed liquor recycle rates to be employed, must be mixed into the separate basins. The overall nitrate removal in the separate basins can then be determined. In this way the overall removal of nitrogen can be determined for each retention time in the first stage and for any recycle rate of mixed liquor.

From experiments conducted, Applicants have found that, on the average, the retention time be at least about 2½ hours in the first stage.

This retention time minimum should only become a factor when the ambient temperature drops below about 20°C. This is supported by the fact that in the experiments which were conducted, as hereinbefore described, the retention time in the first stage was about 2 hours in each case.

In this specification, whenever the retention time is based on the influent flow rate only, it is represented by the symbol $t_q$, and therefore merely gives an indication of the capacity. When the retention time is the actual retention time, it takes into account the recycle rates of mixed liquor and active sludge, and is represented by the symbol $t$.

To illustrate the design of the process of this invention and the inter-relation of the variables for optimum results, reference will be made to the following design example which is included purely by way of example.

For the design of the process of this invention, the following design information should be available:

1. The reduction of C.O.D. (Chemical Oxygen Demand in mg/l) expected $S_r$ or the difference between the C.O.D. of the influent and that of the effluent.
2. The value of the solids yield Y in terms of kg solids per kg C.O.D. removed in the systems. This may also be expressed in terms of kg solids per kg $BOD_5$ (5 day biological oxygen demand in mg/l) or per kg TOC (total organic carbon in mg/l) removed.
3. The rate of endogenous breakdown of biological solids $k_b$ expressed as a fraction of the degradable solids that one reduced per day. This rate is temperature dependent and this dependence should be given in either mathematical or graph form.
4. The rate of denitrification $DN_1$ in the first basin and the rate of denitrification $DN_3$ in the third basin should be known as well as their temperature dependence.
5. The lowest expected liquid temperature T in degrees C in the basin must be determined since this would influence both nitrification and denitrification rates.
6. The highest mixed liquor suspended solids X in mg/l that could be maintained as well as the recycle rate R to maintain this level must be determined.
7. The total nitrogen entering the system usually as total kjeldahl nitrogen (TKN) expressed in mg/l should be determined.
8. The minimum solids retention time (SRT) in the second basin that is required for nitrification at the lowest temperature should be determined.
9. The minimum retention time in the first stage which would result in increased nitrate reduction with increased recycle of mixed liquor.

Assume that the temperature dependence of the denitrification rate and the rate of endogenous breakdown of the biodegradable solids could be expressed by the modified Arrhenius Equation as follows:

$$DN_1(T) = DN_1(20) \theta_1^{(T-20)}$$
$$DN_3(T) = DN_3(20) \theta_1^{(T-20)}$$
$$k_b(T) = k_b(20) \theta_2^{(T-20)}$$

where T and 20 refer to the respective values at T°C and 20°C.

Assume that the following values of the above-mentioned variables were given $S_r(COD) = 400$ mg/l
TKN = 40 mg/l
Y = 0,48 kg solids/kg COD removed
$k_b = 0,1$ per day at 20°C
$DN_1 = 5$ mg $NO_3$-N/g solids/hour
$DN_2 = 1,25$ mg $NO_3$-N/g solids/hour
$\theta_1 = 1,09$
$\theta_2 = 1,08$
T = 14°C
SRT = 12 days
X = 5 000 mg/l
R = 1 times the average dry weather flow The above assumed values are based on the results that are required, the information which is available in the literature, and determinations which have been made and estimated on the basis of experimental work conducted by the Applicants and the experience of the Applicants.

The system consists of four basins in series of which the first basin is anoxic i.e. no air is introduced and nitrates are reduced. These nitrates originate from the second basin from where it is recycled. The remainder of the nitrates i.e. those that are not reduced in the first basin must be reduced in the third anoxic basin. The fourth basin should be designed for re-aeration and have a retention time of about 1 hour based on the average dry weather flow.

One should thus start with the third anoxic basin and then calculate the amount of nitrates remaining in order to calculate the size of the first basin and the recycle rate of mixed liquor from the second to the first basin.

Assume the retention time $t_q(3)$ in the third basin to be 2 hours based on the average dry weather flow rate (adwf).

The actual retention time is $$t = t_q(3)/(1 + R) = 2/2 = 1 \text{ hour}$$

The denitrification rate in the third basin $$DN_3(14°C) = 1,25 \times (1,09)^{(14-20)}$$
$$= 0,74 \text{ mg } NO_3\text{—N/g solids/hr.}$$
$$\text{At X} = 5000 \text{ mg/l}$$

Nitrates removed in this basin

= 0,74 × 5 × 1 = 3,70 mg/l

However, approximately 1 mg/l dissolved oxygen would also pass on to the third basin. The equivalent nitrate nitrogen is 1/2,9 = 0,345 mg/l. Thus the nitrate nitrogen concentration in the third basin $$Cn = 3,70 - 0,35$$
$$= 3,35 \text{ mg/l}.$$

The nitrate concentration in the second basin should thus not exceed 3,7 mg/l. The ammonia in the influent will not be affected by the first basin but will be almost completely nitrified in the second basin. A fraction of the total nitrogen entering the system will be incorporated in the sludge wasted from the unit. A small fraction of the ammonia will not be nitrified and some non-degradable organic matter in solution will contain nitrogen.

About 10 percent of the total nitrogen entering the system will not appear as nitrates anywhere in the process. Thus total nitrogen to be nitrified would be $$Cn_o = 0,9 \times TKN$$
$$= 0,9 \times 40$$
$$= 36 \text{ mg/l based on adwf.}$$

Assuming unit flow rate and considering a balance of nitrates into and out of the second basin, it is clear that the mixed liquor recycle to the first basin $R_r$ should be such that $$[1 + R + R_r].Cn = Cn_o$$

Solve for $R_r$ $$R_r = \frac{Cn_o}{Cn} - 1 - R$$
$$= 36/3,35 - 2$$
$$= 10,7 - 2$$
$$= 8,7$$
$$DN_1 (14°C) = 5 \times (1,09)^{14-20}$$
$$= 2,96 \text{ mg } NO_3-N/g \text{ solids/hr}$$

At a recycle rate of 8,7 times the influent rate and a sludge recycle rate equal to the influent rate, the nitrate concentration entering the first basin would be Cn = 3,35 mg/l. Assume that 1 mg/l dissolved oxygen would be recirculated to the first basin which is equivalent to 0,35 mg/l $NO_3$—N. To calculate the retention time of the first basin, the equivalent of Cn = 3,70 mg/l would be recycled. The actual retention = 3,70/2,96 × 1/5 = 0,25 hour.

Based on the influent flow rate the retention time will be 0,25 × 10,7 = 2,675 hours. This is in excess of the minimum requirements as hereinbefore discussed.

The retention time in the first basin is longer than that in the third basin. Try to find a solution that would result in the minimum basin requirements. Recalculate with the third basin having a retention time of 2,4 hours based on the influent flow rate.

$$C_n = 0,74 \times 5 \times 1,2$$
$$= 4,44 \text{ mg/l}$$
$$R_r = \frac{36}{4,44} - 2$$
$$= 8,2 - 2$$
$$= 6,2 \text{ mg/l}.$$

Actual retention time = 4,44/2,96 × 1/5 = 0,30 Retention time based on influent flow rate = 2,46 hours. Thus assume the basin to have the minimum volume of 2,5 hours retention. Thus a recycle rate of approximately 6 to 1 would be required. This value could obviously be reduced in summer since more nitrates would be reduced in the third basin. Also, if the removal of nitrates to zero would not be required in winter but a value of say 2 mg/l in the effluent would be acceptable, then, taking the last example again, $$Cn = 4,44 + 2 = 6,42$$
$$R_r = \frac{36}{6,42} - 2$$
$$= 5,6 - 2$$
$$= 3,6.$$

Thus a recycle rate of 4 times the influent rate would suffice. The retention time in the first basin based on the flow rate would be $$t_q(1) = 6,42 \times 5,6/2,96 \times 1/5 = 2,42 \text{ hours.}$$

Thus no matter what the recycle rate or the admissable nitrates in the effluent, the retention times in the first and third basins will be approximately 2½ hours each.

The second basin must be based on the requirements for nitrification and the retention time of the solids in this basin should be more than the minimum required for nitrification. The basin size must be determined by a trial and error procedure.

Let the size of the second basin based on the influent flow rate $t_q$ (2) = 6 hours. The total retention time in the whole system would be the sum of the retention times of the four basins.

| Thus $t_q$ | = | $t_q(1) + t_q(2) + t_q(3) + t_q(4)$ |
|---|---|---|
| | = | 2,5 + 6,0 + 2,5 + 1,0 |
| | = | 12 hours. |

The retention time of 6 hours which was taken above for the second basin, was selected by trial and error and from the experience of the Applicants in this field. Similarly, the retention time of 1 hour for the fourth basin was arbitrarily selected on the basis of the experience of the Applicants in this field.

The daily sludge production in the system can be determined from the equation given by Barnard et al. (Barnard, J. L. et al. 'Design Optimization for activated sludge and extended aeration plants' Presented at 6th International Conference of IAWPR in Jerusalem.)

$$\Delta X = Y.S_r - k_b.X.X. t_q$$

where $\Delta X$ = daily sludge production as mg/l of the flow rate
$X$ = biodegradable fraction of the biomass in the basins.

The value of X can be determined from the equation $$x = \frac{Y.S_r + k_b.X.t_q - \sqrt{(Y.S_r + k_b.X.t_q)^2 - 3,08 \, Y.S_r.k_b.X.t_q}}{2k_b.X.t_q}$$

However $k_b$ is also temperature dependent and $$k_b(14°C) = 0,1 \times (1,08)^{14-20}$$

-continued
= 0.063

Thus $$Y.S_r + k_b.X.t_q = 0{,}48 \times 400 + 0{,}063 \times 5000 \times \frac{12}{24}$$
$$= 192 + 158$$
$$= 350$$
$$x = \frac{350 - \sqrt{122\,500 - 3{,}08 \times 192 \times 158}}{2 \times 158}$$
$$= 0{,}56$$
$$\Delta x = 192 - 158 \times 0{,}56$$
$$= 103 \text{ mg/l}$$

The solids retention time in the second basin is thus SRT = 5000 × 6/103 × 24 = 12,1 days which is sufficient for nitrification.

The total retention time is thus 12 hours, of which 2,5 hours in the first basin, 6 hours in the second basin, 2,5 hours in the third basin and 1 hour in the last basin. Since this was assumed in a calculation the mixed liquor suspended solids would need to be 5,000 mg/l and the mixed liquor return should be between 4 and 8 depending on the final effluent requirements.

METHANOL ADDITION TO THIRD BASIN

Methanol may be added to the third basin to enhance denitrification at lower temperatures. The quantity of methanol would depend on the degree of denitrification required. Since most of the nitrates would be removed in the first basin, the methanol requirements would be less than one fifth of that required for total denitrification and this would be required only during the colder months of the year. According to McCarty, P. L. et al. 'Biological denitrification of wastewaters by addition of organic materials' Proc. of 24th Ind. Waste Conf. Purdue University, the rate of methanol addition would be approximately 3 times the rate of nitrate-nitrogen removal. The removal of additional 4 mg/l of nitrate-nitrogen in the third basin would require the addition of 12 mg/l methanol. The COD of the methanol should be added to the total COD removal in the plant for the calculation of the minimum SRT for nitrification.

The COD of methanol can be calculated from the equation $$2\, CH_3OH + 3O_2 = 2\, CO_2 + 4H_2O$$

1 mg/l methanol has a COD value of 1,4 mg/l. Thus adding 12 mg/l methanol would result in an increase of about 17 mg/l of COD.

The actual methanol addition will vary according to the temperature and to the economics of plant construction. A least cost solution should thus be arrived at. The cost of additional basin volume for denitrification and pumping costs should be weighed against the cost of methanol.

Taking the above example and fixing the retention time of the first and third basins at 2 hours each and the recycle rate at 3 times the inflow rate, the effluent nitrate-nitrogen concentration can be calculated as follows.

Nitrate concentration in third basin would be diluted five times, due to mixed liquor recirculation and sludge return. The nitrate concentration would thus be 36/5 or 7,2 mg/l if total denitrification takes place in the first basin. The rate of denitrification in the first basin is 2,96 × 5 = 15 mg/l/hour. The retention time $$t_q(1) = 2/5 = 0{,}4 \text{ hours}$$

maximum denitrification = 15 × 0,4
= 6 mg/l.

At a recycle rate of 3 times the average flow, this would result in a removal of 6 × 3 = 18 mg/l. Thus only 18 mg/l of nitrate will be removed and another 18 mg/l would need to be removed by methanol or the recycle rate must be increased. Since the methanol requirements would be about 3 times the nitrate nitrogen to be removed, it would be necessary to add approximately 54 mg/l of methanol to the third basin to remove the residual nitrate nitrogen. This cost can therefore be weighted against the additional cost of increasing the capacities of the denitrification basins and/or increasing the recycle rate of mixed liquor. In this way a cost solution can be arrived at.

It will be noted from the above design example, that the first to fourth stages have been referred to therein as the first to fourth basins.

It will further be noted from the above design example that, in the manner illustrated, the process can be designed for particular applications.

What I claim is:
1. A process for removing nitrogen from organic waste water containing nitrogenous compounds, which includes the steps of
   a. feeding waste water to a first stage,
   b. passing active sludge recycled from a subsequent stage of the process, to the first stage and inducing turbulence in the first stage for mixing the waste water and the active sludge to provide a mixed liquor, said first stage being a biological denitrification stage for allowing heterotrophic bacteria in suspension in the active sludge to convert nitrates to nitrogenous gases under anoxic conditions,
   c. passing mixed liquor from the first stage to a second stage,
   d. aerating the second stage to maintain aerobic conditions with a dissolved oxygen concentration of between 0.2 and about 6 mg/l, to obtain biological nitrification of nitrogenous compounds to nitrates by nitrifying bacteria contained in the active sludge in the mixed liquor,
   e. recycling mixed liquor containing nitrates formed in the second stage to the first stage at an average daily rate of at least 0.8 by volume of the rate of feed of waste water fed to the first stage,
   f. providing a sufficient residence time of mixed liquor in the first stage in relation to the respiration rate of bacteria in the active sludge in the first stage, to obtain denitrification of at least 80% by weight of the nitrates in the mixed liquor recycled to the first stage,
   g. passing mixed liquor from the second stage to a third stage and inducing turbulence in the third stage, while allowing a sufficient residence time of the mixed liquor in the third stage for endogenous respiration of bacteria in the active sludge, to reduce any oxygen in the mixed liquor and then reduce nitrates to nitrogen gas to remove at least 60% by weight of the nitrates in the mixed liquor entering the third stage from the second stage, h. passing mixed liquor from the third stage to a solids separation stage to provide a clarified effluent and an active sludge having a concentrated suspension of bacteria, i. withdrawing clarified effluent from the solids separation stage, j. recycling at least a portion of the active sludge from the solids separation stage to the first stage to provide the recycled active sludge in the first stage, the active sludge being recycled at a sufficient rate to maintain suspended solids concentration in the mixed liquor of at least about 1,000 mg/l in the first, second and third stages, and k. wasting sludge at a daily rate of less than 16% by weight of the weight of the sludge in all the stages of the process so as to ensure a sufficient residence time of nitrifying bacteria in the second stage, in relation to their growth rate, to prevent washing out of the nitrifying bacteria at a rate faster than their growth rate.

2. A process for removing nitrogen from organic waste water containing nitrogenous compounds, which includes the steps of a. feeding waste water to a first stage, b. passing active sludge recycled from a subsequent stage of the process, to the first stage and inducing turbulence in the first stage for mixing the waste water and the active sludge to provide a mixed liquor, said first stage being a biological denitrification stage for allowing heterotrophic bacteria in suspension in the active sludge to convert nitrates to nitrogenous gases under anoxic conditions, c. passing mixed liquor from the first stage to a second stage, d. aerating the second stage to maintain aerobic conditions, to obtain biological nitrification of nitrogenous compounds to nitrates by nitrifying bacteria contained in the active sludge in the mixed liquor, e. passing mixed liquor from the second stage to a third stage and inducing turbulence in the third stage while allowing a sufficient residence time of the mixed liquor in the third stage for endogenous respiration of bacteria in the active sludge, to reduce any oxygen in the mixed liquor and then reduce nitrates to nitrogen gas to remove at least 60% by weight of the nitrates entering the third stage with the mixed liquor from the second stage, f. recycling mixed liquor containing nitrates formed in the second stage, from the second stage to the first stage at a sufficient rate to maintain the level of nitrates passing from the second stage to the third stage with the mixed liquor, below the level where at least 60% by weight of the nitrates entering the third stage can be removed by the endogenous respiration of the bacteria in the third stage, g. providing a sufficient residence time of mixed liquor in the first stage in relation to the respiration rate of bacteria in the active sludge in the first stage, to obtain denitrification of a major proportion of the nitrates recycled from the second stage to the first stage with the recycled mixed liquor, h. passing mixed liquor from the third stage to a solids separation stage to provide a clarified effluent and an active sludge having a concentrated suspension of bacteria, i. withdrawing clarified effluent from the solids separation stage, j. recycling at least a portion of the active sludge from the solids separation stage to the first stage to provide the recycled active sludge in the first stage, the active sludge being recycled at a sufficient rate to maintain an effective bacterial population level for nitrification and denitrification in the first, second and third stages, k. wasting sludge from the process at a sufficiently low level to provide a sufficient residence time of nitrifying bacteria in the second stage, in relation to their growth rate, to prevent washing out of the nitrifying bacteria at a rate faster than their growth rate.

3. A process according to claim 2, in which aeration of the second stage is controlled to maintain a dissolved oxygen concentration of between 0.5 and 4 mg/l in this stage.

4. A process according to claim 3, in which the dissolved oxygen concentration is maintained between 0.5 and 2 mg/l.

5. A process according to claim 3, which includes the step of providing a suitable carbon source in the third stage to improve the respiration rate of facultative bacteria in the active sludge in the third stage.

6. A process according to claim 5, in which the carbon source is selectively provided in relation to the decrease in the respiration rate of the facultative bacteria.

7. A process according to claim 2, in which the mixed liquor is recycled from the second stage to the first stage at an average daily rate at least equal by volume to the rate of feed of waste water fed to the first stage.

8. A process according to claim 7, in which the mixed liquor is recycled from the second stage to the first stage at an average daily rate of at least 2:1 by volume of the rate of feed of waste water to the first stage.

9. A process according to claim 7, in which the mixed liquor is recycled from the second stage to the first stage at an average daily rate of at least 4:1 by volume of the rate of feed of waste water to the first stage.

10. A process according to claim 2, in which the active sludge is recycled from the solids separation stage to the first stage at a rate sufficient to provide a mixed liquor suspended solids concentration of between about 2,000 and 8,000 mg/l in the first, second and third stages.

11. A process according to claim 10, in which the active sludge is recycled at a rate sufficient to provide a mixed liquor suspended solids concentration of about 4,000 mg/l in the first, second and third stages.

12. A process according to claim 2, in which sludge is wasted from the process at a daily rate of less than about 12% by weight of the weight of the sludge in all the stages of the process.

13. A process according to claim 12, in which the sludge is wasted at a daily rate of between about 3 and 6% by weight of the weight of the sludge in all the stages of the process.

14. A process according to claim 12, in which the sludge is wasted from the active sludge of the solids separation stage.

15. A process according to claim 2, which includes the step of interposing a fourth stage between the third stage and the solids separation stage, and aerating the fourth stage to stabilise the sludge to facilitate solids separation in the solids separation stage.

16. A process according to claim 15, which includes the steps of, where the organic waste water contains phosphates, aerating the fourth stage to maintain a dissolved oxygen concentration of at least 3 mg/l in the fourth stage to obtain phosphate precipitation, and of regularly wasting active sludge from the solids separation stage to remove phosphates from the organic waste water.

17. A process according to claim 16, in which the fourth stage is aerated to maintain a dissolved oxygen concentration of at least 4 mg/l in the fourth stage.

18. A process according to claim 16, which includes the step of subjecting the wasted active sludge from the solids separation stage, to a sludge treatment process to provide a waste stream containing phosphates.

* * * * *